United States Patent [19]

Iwamoto

[11] Patent Number: 5,738,808
[45] Date of Patent: Apr. 14, 1998

[54] HUMIDIFIER FOR INHALANT GAS

[75] Inventor: Junjiro Iwamoto, Yokohama, Japan

[73] Assignees: Asahi Glass Company Ltd., Tokyo; Asahi Glass Engineering Co., Ltd., Ichihara, both of Japan

[21] Appl. No.: 888,505

[22] Filed: Jul. 7, 1997

Related U.S. Application Data

[63] Continuation of Ser. No. 624,916, Mar. 27, 1996, abandoned.

[30] Foreign Application Priority Data

Mar. 31, 1995 [JP] Japan ................................. 7-076127

[51] Int. Cl.⁶ ....................................................... B01F 3/04
[52] U.S. Cl. ........................................ 261/104; 128/204.13
[58] Field of Search ............................ 261/104; 210/638; 128/204.13

[56] References Cited

U.S. PATENT DOCUMENTS

| | | | |
|---|---|---|---|
| 4,098,852 | 7/1978 | Christen et al. | 261/104 |
| 4,101,294 | 7/1978 | Kimura | 261/104 |
| 4,155,961 | 5/1979 | Benthin | 261/104 |
| 4,355,636 | 10/1982 | Oetjen et al. | 261/104 |
| 4,367,734 | 1/1983 | Benthin | 261/104 |
| 4,381,267 | 4/1983 | Jackson | 261/104 |
| 5,273,689 | 12/1993 | Hamasaki | 261/104 |
| 5,300,228 | 4/1994 | Sugaya et al. | 210/638 |
| 5,348,691 | 9/1994 | McElroy et al. | 261/104 |

FOREIGN PATENT DOCUMENTS 2-99113  4/1990  Japan .

Primary Examiner—Tim R. Miles
Attorney, Agent, or Firm—Oblon, Spivak, McClelland, Maier & Neustadt, P.C.

[57] ABSTRACT

A humidifier for an inhalant gas, which humidifies an inhalant gas having a controlled composition without invasion of bacteria by bringing a stream of the inhalant gas into contact with one side of a water vapor-permeable membrane which is in contact with liquid water on the other side.

10 Claims, 1 Drawing Sheet

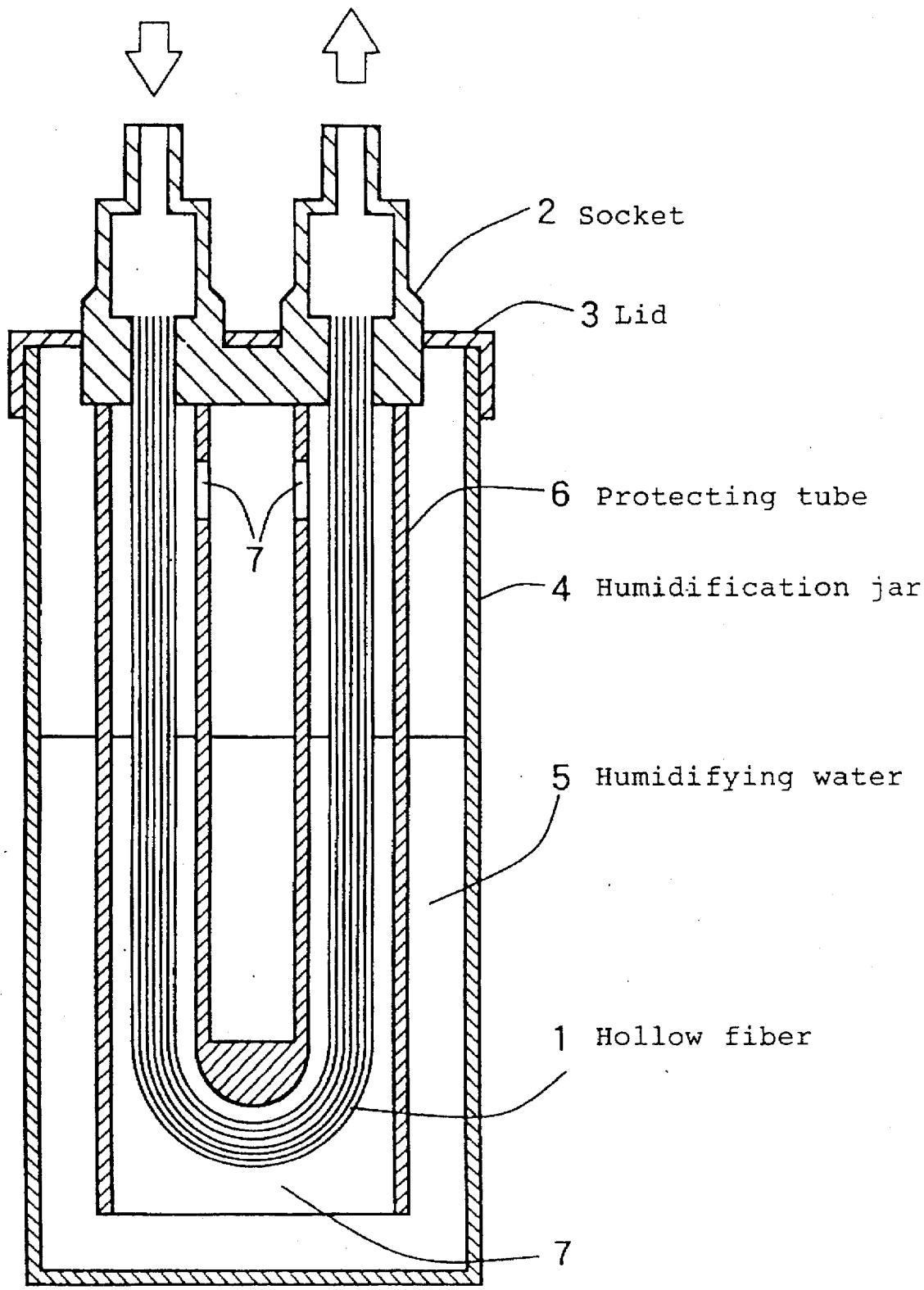

HUMIDIFIER FOR INHALANT GAS

This application is a continuation of application Ser. No. 08/624,916, filed on Mar. 27, 1996, now abandoned.

BACKGROUND OF THE INVENTION

1. Field of the Invention

The present invention relates to a humidifier for an inhalant gas, in particular, a humidifier for an inhalant gas for medical use such as oxygenated air and anesthetic gas-containing air.

2. Discussion of Background

Inhalant gases having artificially controlled compositions such as oxygenated air and anesthetic gas-containing air for medical use, can have various harmful effects, when supplied to a human without any treatment, because of their small water contents. For this reason, inhalant gases are usually humidified to a relative humidity of from 20 to 90% before use.

Heretofore, inhalant gases have been humidified by using a bubbler and directly blown into water. An inhalant gas supplied to a bubbler forms bubbles in water, and the bubbles burst on the water surface with a noise of explosion. Therefore, there are drawbacks that a humidifier must be kept away from an inhaler and that a soundproof facility is necessary.

Further, incorporation of water mist into an inhalant gas at the time of humidification causes troubles such as fluctuation in transfer of the inhalant gas due to water droplets collected in a pipeline between a humidifier and an inhaler, and entrance of water droplets to a human body. Although bubbler-type humidifiers have much space above the water surface to prevent incorporation of water mist, it is difficult to completely prevent incorporation of water mist.

In general, water used for humidification is likely to be contaminated with substances and bacteria in the air. In particular, fungi and bacteria not only contaminate the water but also propagate rapidly in the water in certain conditions. Therefore, incorporation of these contaminants into an inhalant gas can cause a serious accident. To prevent it, sterilized water is used as the humidifying water supplied in a bubbler. However, use of sterilized water as the humidifying water requires cumbersome operations, and, in addition, it is difficult to completely prevent an accident by use of sterilized water, when some fungi are originally clinging to the container. The safest method is to use a sealed disposable bubbler containing sterilized water. However, this method has a problem that when a long term use is taken into consideration, an extremely large financial load is required.

The object of the present invention is to provide a humidifier for an inhalant gas with a low noise which does not generate water mist and is free from contamination of the inhalant gas by contaminants and bacteria.

SUMMARY OF THE INVENTION

The present invention provides a humidifier for an inhalant gas, which humidifies an inhalant gas having a controlled composition without invasion of bacteria by bringing a stream of the inhalant gas into contact with one side of a water vapor-permeable membrane which is in contact with liquid water on the other side.

BRIEF DESCRIPTION OF THE DRAWING

FIG. 1 is cross-sectional view of a humidifier used in Example 2.

DETAILED DESCRIPTION OF THE PREFERRED EMBODIMENTS

In the present invention, a water vapor-permeable membrane means a membrane which is permeable to water vapor but impermeable to liquid water.

Hydrophobic porous substances, when having sufficiently small pore diameters can be used as the above-mentioned water vapor-permeable membrane, because they are permeable to water vapor and have barrier properties to water, namely have selectivity for water vapor, and have barrier properties to bacteria while they basically transmit only water vapor evaporated from the water side of the interface. Hydrophobic porous substances initially exhibit good selectivity for water vapor through such mechanisms, but are likely to become hydrophilic and lose selectivity for water vapor due to generation and adhesion of scale and algae inside them. For this reason, the water vapor-permeable membrane to be used in the present invention is preferred to be a substantially non-porous water vapor-permeable membrane. The term, non-porous, used here means substantially not having pores of 0.1 μm or larger through which bacteria can pass. Concretely, a membrane having a Gurley number of at least 60 seconds is preferable. More preferred are those having a Gurley number of at least 180 seconds.

The water vapor transmission rate is preferably at least 10 g/m$^2$·hr·mmHg, more preferably at least 20 g/m$^2$·hr·mmHg.

In order to be both non-porous and permeable to water vapor, the membrane is preferably composed mainly of a water-containing polymer having a hydrophilic group. For a practical water vapor permeability, the water content of the membrane is preferably at least 1 wt %, more preferably at least 5 wt %, when the membrane is immersed in water at room temperature. However, too high a water content results in poor strength and poor durability. Therefore, the water content at room temperature is preferably at most 100%, more preferably at most 50%.

As such a material, cellophane, a permeable urethane having a hydrophilic group on the polymer chain, an ion exchange polymer having a basic or acidic group on the polymer chain and the like may be mentioned. Among them, ion exchange polymers are preferable, because their strength little decreases due to increase in water content and their high water and chemical resistances permit their stable use.

The material of the ion exchange polymer may, for example, be a styrene-type resin, a ethylene-type resin, a polysulfone-type resin or a fluorine-containing resin. Particularly, a fluorine-type ion exchange resin having fluorine atoms in the polymer chain is a material suitable for this purpose, because it not only has a large permeability to water vapor but also has high strength even when immersed in water and in addition, avoids propagation of bacteria on it. The ion exchange groups of the ion exchange polymer may, for example, be cation exchange groups such as sulfonic acid groups, carboxylic acid groups, phosphoric acid groups, acidic hydroxyl groups or their salt forms in which hydrogen ions are substituted with other cations, or anion exchange groups such as primary to tertiary amino groups or quaternary ammonium groups. Among them, sulfonic acid groups are particularly preferred, since they have high water absorptivity and are scarcely deteriorated by chlorinated lime in water, and excellent in heat resistance and chemical resistance. As the material of ion exchange polymer, a fluorine-containing resin having sulfonic acid groups as ion exchange groups is particularly preferable, because it is excellent in heat resistance, chemical resistance, moldability and mechanical properties.

The ion exchange capacity is preferably from 0.6 to 2.5 meq/g dry resin, to obtain an ion exchange membrane having an excellent water vapor transmission rate and a high membrane strength. The ion exchange capacity is more preferably from 1.0 to 2.0 meq/g dry resin.

A water-containing polymer usually has altered dimensions and reduced strength, when impregnated with water. Therefore, it is preferably used as a laminate with a porous support. As the support, cloth, a non-woven fabric, a porous substance, a mesh and combinations thereof may be used. The porous support preferably has a pore diameter of from 0.01 to 100 μm and a thickness of from 10 to 500 μm, and preferably has hydrophilic surfaces and hydrophilic inner walls. When the base material itself is not hydrophilic, it may be optionally be treated to make it hydrophilic.

Any porous substrate having durability with respect to dimensional stability against water, mechanical strength, chemical resistance and mildew resistance may be used without any particular restrictions. For example, fluoropolymers such as a polytetrafluoroethylene, a tetrafluoroethylene-ethylene copolymer and polyvinylidene fluoride, olefin-type polymers such as polyethylene and polypropylene and a woven fabric and a non-woven fabric made of carbon fibers may be mentioned.

The shape of the membrane is not particularly limited. Water is introduced to one side of a water vapor-permeable membrane in the form of a hollow fiber or of a bag made of a planar water vapor-permeable membrane, while an inhalant gas is passed on the other side. Water transmits through the water vapor-permeable membrane in the state of water vapor to humidify the inhalant gas. In the case of a hollow fiber structure, it is possible to pass water inside the hollow fibers and pass the inhalant gas outside, and vice versa. It is preferable to pass the gas inside the hollow fibers in view of ease of supplying water.

Since no bubbles are formed, this system is free from a noise due to burst of bubbles and from incorporation of mist. In this system, water may be supplied continuously or when it falls short of water.

In the present invention, an inhalant gas means a gas supplied to a human for the purpose of treatment, such as oxygenated air and anesthetic gas. The relative humidity of the humidified gas is preferably from 20 to 90%. Particularly, air oxygenated by a PSA (pressure swing adsorption) system is preferred.

EXAMPLE 1

A copolymer of $CF_2=CFOCF_2CF(CF_3)OCF_2CF_2SO_2F$ with tetrafluoroethylene was molded into a planar membrane having a thickness of 80 μm through an extruder. The planar membrane was hydrolyzed with a potassium hydroxide aqueous solution and treated with hydrochloric acid to convert $—SO_2F$ at the terminals into $—SO_3H$. Thereby, an ion exchange membrane having an ion exchange capacity of 1.1 meq/g dry resin was obtained.

This membrane was immersed in deionized water for 5hours and weighed. Then it was dehydrated in a vacuum dryer at 20 Torr, at 60° C. for 16 hours and weighed again to determine the water content. As a result, the water content was 21 wt %. The Gurley number of this membrane was 300 seconds.

This membrane was fastened in a frame of 20 mm×100 mm and set in a cell so as to partition the cell into two. One of the compartments of the cell was filled with humidifying water, and oxygenated air obtained by a PSA-type medical oxygenation system was introduced to the other compartment at 5 l/min. The relative humidity of the oxygenated air obtained from the oxygenation system was lower than 5%, and the oxygenated air exhaled from the outlet of the cell was humidified to a relative humidity of 55% without any noise due to burst of bubbles and incorporation of water mist.

EXAMPLE 2

The copolymer obtained in Example 1 was molded into hollow fibers each having an inner diameter of 400 μm and an outer diameter of 550 μm. The hollow fibers were treated in the same manner as in Example 1 to convert $—SO_2F$ at the terminals into $—SO_3H$. The ion exchange capacity was 1.1 meq/g dry resin. By using the hollow fibers, a humidifier as shown in FIG. 1 was fabricated. 50 hollow fibers 1 were bundled and bent in a U-shape, and the both ends were fixed in a resin socket 2 with an epoxy resin. Then, the socket 2 was fitted in a lid 3 of a humidification jar, and the humidification jar 4 was lided so that the hollow fibers 1 were immersed in humidifying water 5 in the humidification jar 4. The hollow fibers were packed in a protective tube 6. The protective tube 6 had openings 7 both at the top and at the bottom so that the humidifying water came inside and came into contact with the hollow fibers 1.

Then, oxygenated air obtained by means of a PSA-type medical oxygenation system was introduced into one of the sockets at 5 l/min. The relative humidity of the oxygenated air obtained from the oxygenation system was lower than 5%, and the oxygenated air exhaled from the outlet of the humidification jar was satisfactorily humidified as shown in Table 1, without noise and incorporation of water mist.

TABLE 1

| Level of humidifying water (cm) | Relative humidity of the air from the outlet (%) |
| --- | --- |
| 20 | 62 |
| 40 | 63 |
| 60 | 65 |
| 80 | 67 |
| 100 | 70 |

A culture medium was poured into a petri dish, and bacteria in the air were inoculated in the medium and cultured at 35° C. for 18 hours. The bacteria were added to sterilized distilled water together with the medium to obtain bacterial water. The bacterial water was added to the humidifying water to obtain contaminated humidifying water. 100 cc of the contaminated humidifying water was taken out and filtered through a membrane filter. The membrane filter was placed on an agar medium at 35° C. for 3 days for cultivation of bacteria, and the colonies were counted by using a colony counter. The number of the colonies was $500×10^9$. By using the contaminated humidifying water, an inhalant gas was humidified for 1 hour, while the humidified inhalant gas was introduced in physiological saline. The physiological saline was filtered through membrane filter, and the membrane filter was placed on an agar medium at 35° C. for 3 days for cultivation. No bacterial colonies were observed.

COMPARATIVE EXAMPLE

Oxygenated air exhaled from the same medical oxygenation system as in Example 1 at 5 l/min. was humidified through a humidification bubbler. The bubbler made a noise attributable to burst of bubbles. In addition, when the bubbler was full of humidifying water, the oxygenated air carried mist, and water droplets collected in a tube connected to the bubbler. Then, humidification was carried out for an hour after the humidifying water was contaminated in the same manner as in Example 2, and the bacterial colonies were counted. The number of the colonies was $23 \times 10^2$. 100 cc of the contaminated humidifying water was taken out and the bacterial colonies were counted in the same manner. As a result, the number of the colonies was $17 \times 10^9$.

The humidifier of the present invention can humidify an inhalant gas without noise, incorporation of water mist and invasion of bacterial. Therefore it requires neither sterilized water as the humidifying water nor a disposable container and is sanitarily safe.

What is claimed is:

1. A humidifier for an inhalant gas, comprising:
   (a) a container for containing liquid water and a lid with sockets therein fitted on the top of the container;
   (b) a plurality of hollow fibers of a water-permeable membrane which are bent into a U-shape, and wherein each end of the U-shape is adapted to fit in a socket;
   (c) means for bringing a stream of an inhalant gas having a controlled composition into contact with the inside of the hollow fibers through said sockets;
   (d) a protective tube in which the hollow fibers are packed and placed in said container, said protective tube containing at least one opening sufficient to allow said liquid water to contact at least a part of said hollow fibers.

2. The humidifier according to claim 1, wherein the lid and sockets are out of contact with liquid water.

3. The humidifier according to claim 1, wherein the water vapor-permeable membrane is composed mainly of a water-containing polymer having a hydrophilic group and has a water content of from 1 to 100 wt %.

4. The humidifier according to claim 1, which humidifies the inhalant gas to a relative humidity of from 20 to 90%.

5. The humidifier according to claim 1, wherein the water vapor-permeable membrane has a Gurley number of at least 60 seconds.

6. The humidifier according to claim 1, wherein the water vapor-permeable membrane has a water vapor transmission rate of at least 10 $g/m^2 \cdot hr \cdot mmHg$.

7. The humidifier according to claim 1, wherein the inhalant gas having a controlled composition is oxygenated air.

8. The humidifier according to claim 7, wherein the oxygenated air is obtained by oxygenating air by a pressure swing adsorption system.

9. The humidifier according to claim 1, wherein the water vapor-permeable membrane is made of an ion exchange polymer.

10. The humidifier according to claim 9, wherein the ion exchange polymer is a fluoro-containing resin having sulfonic acid groups as ion exchange groups.

* * * * *